US010023520B2

(12) United States Patent
Horstmann et al.

(10) Patent No.: US 10,023,520 B2
(45) Date of Patent: Jul. 17, 2018

(54) PREPARATION OF TERT-BUTYL ESTERS OF ALIPHATIC CARBOXYLIC ACIDS

(71) Applicant: BASF SE, Ludwigshafen am Rhein (DE)

(72) Inventors: Catharina Horstmann, Ilvesheim (DE); Claus Hechler, Ludwigshafen (DE); Gregor Grackiewicz, Ludwigshafen (DE); Bernd Schall, Eich (DE)

(73) Assignee: BASF SE, Ludwigshafen am Rhein (DE)

( * ) Notice: Subject to any disclaimer, the term of this patent is extended or adjusted under 35 U.S.C. 154(b) by 27 days.

(21) Appl. No.: 15/086,715

(22) Filed: Mar. 31, 2016

(65) Prior Publication Data

US 2016/0289159 A1 Oct. 6, 2016

Related U.S. Application Data

(60) Provisional application No. 62/140,473, filed on Mar. 31, 2015.

(30) Foreign Application Priority Data

Mar. 31, 2015 (DE) ........................ 10 2015 205 752

(51) Int. Cl.
*C07C 69/52* (2006.01)
*C07C 67/04* (2006.01)
*C07C 67/54* (2006.01)
*C07C 67/62* (2006.01)

(52) U.S. Cl.
CPC .............. *C07C 67/04* (2013.01); *C07C 67/54* (2013.01); *C07C 67/62* (2013.01)

(58) Field of Classification Search
USPC ...................................................... 560/205
See application file for complete search history.

(56) References Cited

U.S. PATENT DOCUMENTS

| 3,031,495 | A | 4/1962 | Young et al. |
| 3,037,052 | A | 5/1962 | Bortnick et al. |
| 3,082,246 | A | 3/1963 | Chafetz et al. |
| 3,087,962 | A | 4/1963 | Bortnick et al. |
| 3,088,969 | A | 5/1963 | Callahan et al. |
| 2003/0127315 | A1* | 7/2003 | Kroker .................. B01D 1/065 203/29 |
| 2005/0124075 | A1* | 6/2005 | Hammon ................ C07C 51/44 436/181 |

FOREIGN PATENT DOCUMENTS

| DE | 1 128 428 | | 4/1962 |
| DE | 1 249 857 | | 9/1967 |
| DE | 31 05 399 | A1 | 10/1982 |
| EP | 268 999 | A2 | 6/1988 |
| WO | WO 02/10109 | A1 | 2/2002 |
| WO | WO 02/10110 | A2 | 2/2002 |

* cited by examiner

*Primary Examiner* — Sudhakar Katakam
*Assistant Examiner* — Ana Z Muresan
(74) *Attorney, Agent, or Firm* — Oblon, McClelland, Maier & Neustadt, L.L.P.

(57) ABSTRACT

A process for continuously preparing the tert-butyl ester of an aliphatic $C_1$-$C_4$ carboxylic acid comprises: a) the reaction of an aliphatic $C_1$-$C_4$ carboxylic acid with isobutene in the presence of an acidic catalyst to give an esterification mixture (G1); b) the partial evaporation of the esterification mixture (G1), giving a liquid first high boiler phase (SPh1) comprising the acidic catalyst, and a first vapor (B1) comprising tert-butyl ester; c) the fractional condensation of the first vapor (B1) by partially condensing the first vapor (B1) at a first pressure and a first temperature and obtaining a first condensate (K1), partially condensing the uncondensed second vapor (B2) at a second pressure and a second temperature and obtaining a second condensate (K2), the first temperature being 0 to 45° C. below the condensation temperature of the tert-butyl ester at the first pressure and the second temperature being 45 to 80° C. below the condensation temperature of the tert-butyl ester at the second pressure, with the proviso that the second temperature is at least 5° C. below the first temperature; and d) the combination of the first condensate (K1) and the second condensate (K2) and the feeding to a combined workup, and recycling of the third vapor (B3) not condensed at the second temperature into step a). The process allows the preparation of the tert-butyl ester of an aliphatic $C_1$-$C_4$ carboxylic acid by reaction of the carboxylic acid with isobutene, with isolation of unconverted isobutene from the esterification mixture in an energetically favorable manner and with an improved degree of removal.

17 Claims, 1 Drawing Sheet

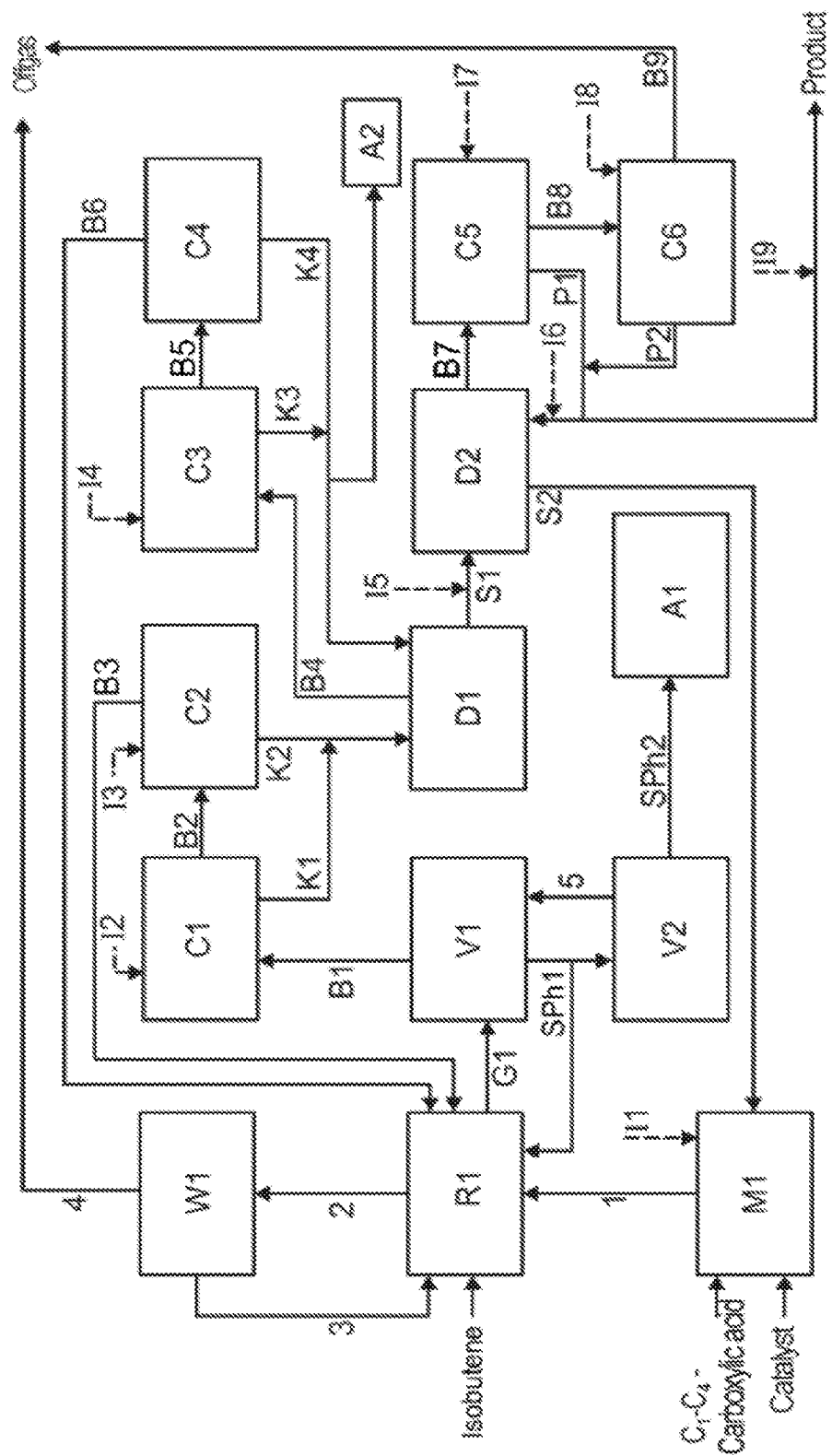

PREPARATION OF TERT-BUTYL ESTERS OF ALIPHATIC CARBOXYLIC ACIDS

The present invention relates to a continuous process for preparing tert-butyl esters of aliphatic $C_1$-$C_4$ carboxylic acid by reacting the carboxylic acid with isobutene.

The tert-butyl esters of aliphatic $C_1$-$C_4$ carboxylic acids have a variety of uses. The tert-butyl esters of saturated aliphatic carboxylic acids such as tert-butyl acetate, for example, are sought-after solvents. tert-Butyl (meth)acrylates are important starting materials for preparation of polymers which are used, inter alia, as a constituent of paints, adhesives or coating resins. tert-Butyl esters are generally prepared by acid-catalyzed addition of a carboxylic acid onto isobutene (Houben-Weyl, Methoden der Organischen Chemie [Methods of Organic Chemistry], vol. 8, 1952, p. 534; U.S. Pat. Nos. 3,031,495 and 3,082,246). Catalysts used are acids soluble in the reaction mixture, for example mineral acids or alkyl- or arylsulfonic acids (DE-A-12 49 857, U.S. Pat. Nos. 3,087,962, 3,088,969), or insoluble catalysts such as acidic exchanger resins (U.S. Pat. Nos. 3,037,052, 3,031,495, DE-A-31 05 399, EP-A-268 999).

WO 02/10109 describes a process for continuously preparing the tert-butyl ester of an aliphatic $C_1$-$C_4$ carboxylic acid by reacting the carboxylic acid with isobutene in the liquid phase in the presence of an acidic catalyst, wherein the reaction is conducted in a reactor divided into a plurality of sections, the carboxylic acid, the isoolefin and catalyst are fed into the first section of the reactor, the resultant reaction mixture is withdrawn from the last section of the reactor and the ester is obtained therefrom, the reaction temperature in the reactor being controlled such that it is within the range from 10 to 40° C. and is at its highest in the first section of the reactor.

WO 02/10110 describes a process for preparing a tert-alkyl (meth)acrylate by reacting (meth)acrylic acid with an olefin in a homogeneous phase in the presence of an acidic catalyst and obtaining the tert-alkyl (meth)acrylate from the reaction mixture, with removal of the catalyst as residue by a two-stage distillation of the reaction mixture and recovery of the tert-alkyl (meth)acrylate from the distillates. WO 02/10110 describes a condensation of the vapors in two series-connected condensers, with the second condenser operated at a lower cooling temperature.

The reaction of the carboxylic acid with isobutene generally does not proceed quantitatively. It is therefore desirable to very substantially separate unconverted isobutene out of the esterification mixture and to recycle it. A problem with the known processes is the fact that the separation of the unconverted isobutene by partial condensation of the vapor obtained in the catalyst removal proceeds with insufficient separation sharpness because of the solubility of the isobutene in the tert-butyl ester. As a result, tert-butyl ester is also recycled back into the synthesis reactor together with the isobutene cycle gas and/or significant amounts of isobutene are removed only in the course of further workup in the purifying distillation of the tert-butyl ester.

It is therefore an object of the invention to provide a process for preparing the tert-butyl ester of an aliphatic $C_1$-$C_4$ carboxylic acid by reacting the carboxylic acid with isobutene, in which unconverted isobutene is isolated from the esterification mixture in an energetically favorable manner and with an improved degree of removal.

The object is achieved by a process for continuously preparing the tert-butyl ester of an aliphatic $C_1$-$C_4$ carboxylic acid, in which:

a) an aliphatic $C_1$-$C_4$ carboxylic acid is reacted with isobutene in the presence of an acidic catalyst to give an esterification mixture (G1);

b) the esterification mixture (G1) is partially evaporated, giving a liquid first high boiler phase (SPh1) comprising the acidic catalyst, and a first vapor (B1) comprising tert-butyl ester;

c) the first vapor (B1) is fractionally condensed by partially condensing the first vapor (B1) at a first pressure and a first temperature and obtaining a first condensate (K1), partially condensing the uncondensed second vapor (B2) at a second pressure and a second temperature and obtaining a second condensate (K2), the first temperature being 0 to 45° C. below the condensation temperature of the tert-butyl ester at the first pressure and the second temperature being 45 to 80° C. below the condensation temperature of the tert-butyl ester at the second pressure, with the proviso that the second temperature is at least 5° C. below the first temperature; and d) the first condensate (K1) and the second condensate (K2) are combined and fed to a combined workup, and the third vapor (B3) not condensed at the second temperature is recycled into step a).

The condensation temperature of a compound refers to the temperature from which the compound condenses at a given pressure, i.e. is converted from the gaseous state of matter to the liquid state. A partial condensation is understood to mean an incomplete condensation, especially a condensation in which, as well as the permanent gases, a portion of the organic compounds also remains in the gas phase. The temperatures stated here for the partial condensations relate to the temperature of the condensate on withdrawal from the particular condenser.

In the first condensation at a temperature at or just below the condensation temperature of the tert-butyl ester, a majority of the tert-butyl ester is condensed out, while a comparatively small amount of isobutene co-condenses. The uncondensed vapor is partially condensed at a lower, second temperature. In the second partial condensation, a proportionately greater amount of isobutene is co-condensed, but the volume flow rate is generally lower. The two-stage partial condensation at a first temperature and a second, lower temperature achieves a higher separation sharpness overall than a one-stage partial condensation. Moreover, the cooling power required in the two-stage partial condensation is generally lower than in a one-stage partial condensation.

The uncondensed vapor comprises isobutene having a high purity level, which can be recycled into the esterification a), while the combined condensates of the fractional condensation include only small amounts of isobutene which are removed in the downstream workup steps.

Esterification

In the esterification a), an aliphatic $C_1$-$C_4$ carboxylic acid is reacted with isobutene in the presence of an acidic catalyst to give an esterification mixture. The aliphatic $C_1$-$C_4$ carboxylic acids are especially formic acid, acetic acid, propionic acid, butyric acid and isobutyric acid. In a preferred embodiment, the carboxylic acid is acrylic acid or methacrylic acid, particular preference being given to acrylic acid.

The process is generally effected in the absence of a solvent and in the liquid phase. Catalysts used are therefore those which are at least partly soluble in the reaction mixture. Suitable catalysts are strong inorganic or organic acids. Strong inorganic acids are, for example, mineral acids such as sulfuric acid, phosphoric acid and polyphosphoric acid, preferably sulfuric acid. Strong organic acids are, for example, sulfonic acids such as p-toluene-, benzene-, dodecylbenzene- and methanesulfonic acid, preferably p-toluenesulfonic acid and methanesulfonic acid. The inorganic catalysts in particular are only partly soluble in the reaction mixture on commencement of the reaction. In the course of the reaction, the solubility of the catalyst improves (primarily because of the formation of a partial ester of the catalyst, for example the sulfuric monoester). At least in the last section, it is therefore generally dissolved in the reaction mixture.

The concentration of the catalyst in the esterification mixture is generally about 0.1% to 10% by weight, preferably 0.5% to 5% by weight, based on the total amount of the esterification mixture.

The reaction of the aliphatic $C_1$-$C_4$ carboxylic acid with isobutene in the presence of an acidic catalyst is effected in conventional reaction vessels or in columns (DE-A-11 28 428). A suitable reactor is described by way of example in WO 02/10109 A1.

Preferably, the reaction is conducted in a reactor, which is especially a cylindrical reactor. The reactor is divided into a plurality of, preferably 3, 4 or 5, separate sections. The sections are separated from one another by dividing walls which run at right angles to the longitudinal axis of the reactor. Each of these has at least one orifice in order to enable the passage of the reaction mixture from one reactor section to the next. The number of orifices per dividing wall is guided by the size of the reactor. Preferably, the dividing walls have one orifice which is especially present in the middle of the dividing wall. The total area of the orifices per dividing wall is about 1/2000 to 1/500 of the cross-sectional area of the reactor.

The volume of the reactor sections may be the same or different. Preferably, the volume of the first reactor section is greater than that of the remaining sections. In the case of a reactor having four sections, the following proportions of the individual sections in the total reactor volume have been found to be preferable:

| | |
|---|---|
| Reactor section 1 | 25% to 50% |
| Reactor section 2 | 10% to 25% |
| Reactor section 3 | 10% to 25% |
| Reactor section 4 | 25% to 50% |

The reactor sections may advantageously be equipped with internals in order to improve the mixing of the reaction volume. Suitable internals are, for example, static mixing elements and internals having similar effects, such as grids, distributor plates or sieve plates. It is particularly preferable to equip the first reactor section with internals of this kind, which are then used especially in the upper half of the reactor section.

The $C_1$-$C_4$ carboxylic acid is fed into the first section of the reactor in liquid form, especially in the region of the base of the reactor. The feeding can be effected directly, for example via an immersed tube, but it is preferable to provide means which enable homogeneous distribution and mixing of the feedstocks. Means of this kind are known to those skilled in the art, for example distillative plates, perforated plates and tubes, nozzles, etc. The $C_1$-$C_4$ carboxylic acid is preferably fed in via a nozzle which brings about the mixing of a gas and a liquid and the mixing of the reactor contents. It is preferably disposed at the base of the reactor. Suitable nozzles are known to those skilled in the art (jet nozzle, mixing nozzle, two-phase nozzle, etc.) and are described, for example, in Ullmann's Encyclopedia of Industrial Chemistry, vol. B4, 5th edition, 1992, p. 280. Especially when a nozzle of this kind is used, the flow in the first reactor sections is turbulent, but is essentially laminar in the downstream reactor sections. This allows the cascading of reaction sections of different characteristics, for example turbulent with high backmixing as in the stirred tank type, or laminar with low backmixing as in the tubular reactor type, which allows particularly advantageous configuration of the respective reaction section.

The catalyst is fed in in a mixture with the carboxylic acid, it being possible to employ fresh catalyst or recovered catalyst or a mixture thereof.

It has been found to be advantageous to feed at least a portion of the liquid high boiler phase from the partial evaporation and/or at least a portion of the bottom product of the purifying distillation described hereinafter into the reactor. In this way, a majority of the acidic catalyst and of the unconverted carboxylic acid is recycled.

The isobutene can be fed in in liquid and/or gaseous form. It is preferably fed in via an annular tube having a plurality of passage orifices.

In addition, it has been found to be advantageous to feed recycled isobutene obtained in the low boiler removal into the first reactor section. When gaseous isobutene is used, it is particularly advantageous to feed in the isobutene together with the carboxylic acid via the nozzle mentioned. The nozzle brings about automatic suction of the gaseous isobutene recycled, using the liquid carboxylic acid as motive medium.

A portion of the reaction mixture can be withdrawn from the first and/or second reactor section and recycled back into the section in question. This assures better mixing of the reaction mixture. The substream is appropriately recycled via the abovementioned mixing nozzle into the first reactor section and/or via a further nozzle in the region of the orifice present in the dividing wall into the second reactor section. The further nozzle may be a nozzle of the type mentioned above for the mixing nozzle. Preference is given to using a conical nozzle. The latter is preferably arranged such that its exit opening is at about the level of the dividing wall which divides the first section from the second. For (closed-loop) control of the temperature, the particular substream withdrawn can be conducted through a heat transferer.

The resultant esterification mixture is withdrawn at the upper end of the reactor and sent to further workup. Unconverted gaseous isobutene accumulates in the upper region of the reactor. Preferably, organic compounds, such as unconverted carboxylic acid, which are condensable are condensed out of the isobutene-containing gas stream taken off at the upper end of the reactor and thus are freed of gases that are inert with respect to the esterification, such as air and butane. Unconverted isobutene dissolves partly in the constituents condensed out. The condensed organic compounds are then fed into the first reactor section in liquid form via the mixing nozzle for example.

The esterification temperature overall is in the range from about 10 to 40° C. It is preferably controlled in such a way that it is at its highest in the first reactor section. Preferably, the reaction temperature in the first reactor section is in the range from about 30 to 40° C. It is lower in the second section, preferably by about 5 to 15° C. The temperature in the sections that follow downstream of the second section may be the same or different. It is generally not higher than in the second section, preferably lower, especially by about 3 to 10° C. In the fourth section, it is generally as high as in the third section or about 1 to 5° C. lower. The temperature in the last reactor section is preferably in the range from about 10 to 25° C.

The temperature distribution in a reactor having 4 sections is preferably as follows:

| | |
|---|---|
| 1st section: | 33 to 38° C. |
| 2nd section: | 23 to 28° C. |
| 3rd section: | 15 to 22° C. |
| 4th section: | 15 to 22° C. |

The temperature in the 3rd and 4th sections may be the same or different.

Since the addition of carboxylic acids onto isobutene is exothermic, it is appropriate to adjust the reaction temperature by removing the heat of reaction, especially in the first two reactor sections. This is especially effected with the aid of heat exchangers which may be in external or internal configuration. Cooling of the reactor walls is also possible. It has been found to be appropriate to undertake the temperature control in the first two reactor sections with the aid of external heat exchangers, through which a substream of the reaction mixture present in the particular reactor section is conducted and recycled again.

The esterification can be conducted at reduced pressure, ambient pressure or slightly elevated pressure (100 to 300 mbar abs.), or preferably at elevated pressure (e.g. 0.5 to 3 bar).

The reaction mixture leaving the reactor comprises a high proportion of the desired ester. In addition, it comprises unconverted reactants, catalyst, stabilizer, esters of the catalyst acid and further minor by-products. The reaction mixture comprises only very small amounts of isobutene oligomerization product, generally <2% by weight, based on the reaction mixture.

Catalyst Removal

To remove the catalyst, the esterification mixture is partially evaporated, giving a liquid high boiler phase comprising the acidic catalyst and a first vapor comprising tert-butyl ester and isobutene. The first vapor additionally comprises small amounts of carboxylic acid and low-boiling constituents (tert-butanol and diisoolefin). The liquid high boiler phase is generally at least partly recycled into the reactor.

The partial evaporation b) can be conducted in any desired manner, but is preferably conducted in two stages. The evaporation is generally effected at elevated temperature and under reduced pressure. The conditions are guided by the particular product desired. They are generally chosen such that the temperature is in the range from about 50 to 150° C. The pressure is adjusted such that the evaporation is rapid and gentle. The pressure is, for example, in the range from 10 to 200 mbar abs., more preferably in the range from 30 to 90 mbar abs., most preferably in the range from 50 to 70 mbar abs.

Any vacuum pumps are suitable for generation of the reduced pressure. To avoid contamination, it has been found to be useful to use lubricant oil-free pumps. Particular preference is given to using Roots vacuum pumps without lubricant oil and what are called dry-running screw vacuum pumps. Alternatively, it is possible to use liquid-ring pumps in which, for example, the target ester serves as barrier fluid.

The two-stage evaporation is preferably conducted in such a way that, in the first stage, 40% to 95% by weight, preferably 60% to 90% by weight, of the desired ester evaporates off. The vapor comprises, as well as the tert-butyl ester and carboxylic acid, the low-boiling constituents such as tert-butanol, tert-butyl acetate and diisobutene. The bottoms obtained in the first distillation comprise, as first high boiler phase, essentially the residual tert-butyl ester, carboxylic acid, acidic catalyst and high-boiling constituents, for example polymeric (meth)acrylic compounds in the case of use of (meth)acrylic acid. 10% to 100% by weight of the first high boiler phase is fed to the second evaporation stage. If only a portion of the first high boiler phase is fed to the second evaporation stage, the remainder of the first high boiler phase is recycled into the reactor. In the second evaporation stage, the residual target ester and the majority of carboxylic acid (up to about 90% by weight) are evaporated off. The vapors from the two stages are combined and conducted onward as first vapor.

The bottoms of the second evaporation stage, as the second high boiler phase, comprise essentially the acidic catalyst, the residual carboxylic acid and high-boiling constituents, for example polymeric (meth)acrylic compounds in the case of use of (meth)acrylic acid. In the two-stage evaporation, it is thus a separation of the reaction mixture into a distillate or first vapor comprising essentially the target ester, carboxylic acid and the low-boiling constituents mentioned, and the residue (second high boiler phase) comprising essentially the acidic catalyst, carboxylic acid and the high-boiling constituents mentioned. The distillate contains generally <20 ppm, especially <10 ppm, of catalyst.

The second high boiler phase is discharged at least partly, preferably fully. However, it can also be partly recycled into the reactor.

Both evaporation stages can be conducted in customary apparatuses. Preference is given, however, to using apparatuses which allow rapid distillation, for example film evaporators. Suitable film evaporators are known to those skilled in the art; see, for example, Ullmann's Encyclopedia of Industrial Chemistry, 5th ed., vol. B3, 2-21 to 2-24 and 3-1 to 3-25, 1988.

Preference is given to using falling-film or falling-stream evaporators in the first evaporation stage, and thin-film evaporators having wipers or helical tube evaporators in the second stage.

It has been found to be particularly preferable to use the falling-film evaporator described by way of example in WO 02/10110 in the first evaporation stage.

Fractional Two-Stage Condensation

According to the invention, a two-stage partial condensation of the first vapor is effected at two different temperatures. This achieves very substantial removal of the tert-butyl ester with minimum co-condensation of unconverted isobutene. The fractional condensation is preferably effected in two series-connected condensers (a first and second condenser), preferably plate or shell and tube condensers. Preference is given to using shell and tube condensers having vertical tubes through which the vapor flows from the top downward.

The first temperature is 0 to 45° C., preferably 5 to 35° C., below the condensation temperature of the tert-butyl ester at the first pressure. The second temperature is 45 to 80° C., preferably 50 to 65° C., even more preferably 50 to 55° C., below the condensation temperature of the tert-butyl ester at the second pressure.

The second temperature is at least 5° C. below the first temperature. Preferably, the second temperature is at least 10° C., more preferably at least 20° C., even more preferably at least 30° C. and most preferably at least 40° C. below the first temperature.

The first temperature is preferably in the range from 15 to 45° C., more preferably in the range from 20 to 40° C. The second temperature is preferably in the range from −10 to −25° C., more preferably in the range from −15 to −22° C.

The first pressure is preferably in the range from 10 to 200 mbar abs., more preferably in the range from 30 to 90 mbar abs., even more preferably in the range from 50 to 70 mbar abs. The second pressure is preferably in the range from 10 to 200 mbar abs., more preferably in the range from 30 to 90 mbar abs., even more preferably in the range from 50 to 70 mbar abs. Usually, the first and second condensers are connected on the gas side. In that case, the first and second pressures are the same.

For example, the condensation temperature of tert-butyl acrylate at 60 mbar abs. is 43° C. In this case, for the cooling of the first condenser, it is appropriately possible to use river water or cooling water at the same temperature level, while the second condenser is operated with brine cooling.

To avoid solid deposits on the contact surfaces of the condenser, a substream of the collected condensate is appropriately circulated, in order to constantly purge the contact surfaces. The condensate pumped in circulation can be distributed homogeneously, for example by means of a distributor, between the tubes of the shell and tube condenser and runs off down the inner walls of the tubes of the condenser. When polymerizable carboxylic acids are used, distribution of a stabilizer described in detail below is also achieved.

The condensate of the first and second condensers can be collected and circulated separately. In general, however, substreams of the combined condensate are pumped into both condensers. In a preferred embodiment, the condensate is fed into the first or second condenser via the feeding vapor pipe in each case. Preferably, the condensate is introduced by jetting into the vapor pipe in the opposite direction to the gas stream, with the nozzle appropriately installed in the vapor pipe in the region of the condenser inlet. The amount of condensate which is recycled into the first condenser is preferably about 5 to 10 times the amount of the stream fed to the further workup. The amount of condensate which is recycled into the second condenser is preferably about 0.1% to 5% of the condensate recycled into the first condenser.

Low Boiler Removal

The combined condensate of the fractional condensation c) is sent to a combined workup. This workup generally comprises a distillative low boiler removal and a purifying distillation. In the distillative low boiler removal, the low-boiling constituents, i.e. constituents other than isobutene having lower boiling points than the target ester, are preferably distilled off overhead. The low boiler removal also affords further amounts of unconverted isobutene which are preferably separated from the low-boiling constituents and are recycled into step a). Low boilers obtained in the preparation of tert-butyl acrylate are, for example, tert-butyl acetate, tert-butanol and diisobutene.

In one embodiment, the low boiler removal is fed with the combined condensate from a first distillation column (D1), giving a first liquid bottom product (S1) and a fourth vapor (B4); the first liquid bottom product (S1) is fed to a further workup; the fourth vapor (B4) is fractionally condensed by partially condensing the fourth vapor (B4) at a third pressure and a third temperature and obtaining a first low boiler condensate (K3), the uncondensed fifth vapor (B5) is partially condensed at a fourth pressure and a fourth temperature and a second low boiler condensate (K4) is obtained, the fourth temperature being lower than the third temperature; the sixth vapor (B6) uncondensed at the fourth temperature is recycled into step a); and the first and/or second low boiler condensate (K3) and (K4) is recycled partly as reflux to the top of the first distillation column (D1).

The two-stage condensation is energetically advantageous since it is possible to use a coolant at a higher temperature level in the first stage. The fourth vapor is cooled in the first stage only to the third temperature below the dew point of the low boilers. Low boilers which remain in the fifth vapor and have not condensed at the third temperature are condensed at the lower fourth temperature. In this way, reduced co-condensation of isobutene is achieved.

The sixth vapor may also still comprise up to 5% by weight, based on the top product, or target ester. The first liquid bottom product comprises essentially target ester and carboxylic acid.

Isobutene in the form of the sixth vapor uncondensed at the fourth temperature is removed and fed to the esterification a). The fractional condensation allows high degrees of purity of the fractions obtained and hence a more efficient process with reduced return streams.

The distillation temperature (bottom temperature) in the first distillation column is generally in the range from 30 to 110° C. The pressure is chosen correspondingly according to the product.

Useful distillation columns are customary columns having random packings or structured packings or having bubble-cap, valve or sieve trays. Preference is given, however, to using a tray column having 30 to 50 dual-flow trays. The feed to the distillation column is generally in the middle region.

The fractional condensation of the low-boiling components is preferably effected in two series-connected condensers (a third and a fourth condenser), especially plate or shell and tube condensers. Preference is given to using shell and tube condensers having vertical tubes through which the vapor flows from the top downward. The temperature of the coolant in the fourth condenser is about 30 to 60° C. lower than that in the third condenser, in which the coolant has a temperature in the range from about 10 to 35° C.

Diisobutene is the main constituent of the low boilers removed. Diisobutene is a mixture of various isooctene isomers. The condensation points thereof are close together in practice. The reference point may, for example, be the condensation point of 2,4,4-trimethylpent-1-ene.

The third temperature is preferably 5 to 40° C., more preferably 7 to 30° C., below the condensation temperature of diisobutene at the third pressure. The fourth temperature is preferably 30 to 55° C., more preferably 35 to 50° C., even more preferably 35 to 45° C., below the condensation temperature of diisobutene at the fourth pressure.

The fourth temperature is at least 5° C. below the third temperature. Preferably, the fourth temperature is at least 10° C., more preferably at least 20° C., even more preferably at least 30° C. and most preferably at least 40° C. below the third temperature.

The third pressure is preferably in the range from 10 to 300 mbar abs., more preferably in the range from 90 to 150 mbar abs., even more preferably in the range from 110 to 130 mbar abs. The fourth pressure is preferably in the range from 10 to 200 mbar abs., more preferably in the range from 90 to 150 mbar abs., even more preferably in the range from 110 to 130 mbar abs. Usually, the third and fourth condensers are connected on the gas side. In that case, the third and fourth pressures are the same.

For example, the condensation temperature of diisobutene at 120 mbar abs. is 40° C. In this case, for the cooling of the third condenser, it is appropriately possible to use river water or cooling water at the same temperature level, while the fourth condenser is operated used with brine cooling.

Purifying Distillation

In the purifying distillation, the target ester is separated from higher-boiling components remaining and is preferably distilled off overhead.

The tert-butyl ester generally boils at lower temperatures than the $C_1$-$C_4$ carboxylic acid. The second liquid bottom product contains unconverted $C_1$-$C_4$ carboxylic acid remaining and is recycled at least partly, especially fully, into the esterification a).

The distillation temperature is generally in the range from 40 to 130° C. The pressure is chosen according to the ester to be distilled.

The second distillation column is typically a conventional tray column, for example a column having 30 to 50 dual-flow trays and a feed in the middle region of the column. The essentially pure target ester is removed via the top of the column.

In one embodiment, the first liquid bottom product (S1) obtained in the low boiler removal is fed to a second distillation column (D2) to obtain a second liquid bottom product (S2) and a seventh vapor (B7); the second liquid bottom product (S2) is at least partly recycled into step a); the seventh vapor (B7) is fractionally condensed by partially condensing the seventh vapor (B7) at a fifth pressure and a fifth temperature and obtaining a first product condensate (P1), the uncondensed eighth vapor (B8) is partially condensed at a sixth pressure and a sixth temperature and a second product condensate (P2) is obtained, the sixth temperature being lower than the fifth temperature; and the first and/or second product condensate (P1) and (P2) is recycled partly as reflux into the second distillation column (D2).

The substreams of the first and second product condensate which are not recycled as reflux into the second distillation column are at least partly discharged from the process as product.

The fractional condensation of the target ester is preferably effected in two condensers arranged in series (a fifth and sixth condenser), especially plate or shell and tube condensers. Preference is given to using shell and tube condensers having vertical tubes through which the vapor flows from the top downward. The two-stage condensation is energetically advantageous since it is possible to use a coolant at a higher temperature level in the first stage. The seventh vapor is cooled in the first stage only to the fifth temperature below the dew point of the target ester. Target ester which remains in the eighth vapor and has not condensed at the fifth temperature is condensed at the lower sixth temperature.

To avoid solid deposits on the contact surfaces of the condenser, a substream of the collected condensate is appropriately circulated, in order to constantly purge the contact surfaces. The condensate pumped in circulation can be distributed homogeneously, for example by means of a distributor, between the tubes of the shell and tube condenser and runs off down the inner walls of the tubes of the condenser. When polymerizable carboxylic acids are used, distribution of a stabilizer described in detail below is also achieved.

The condensate of the fifth and sixth condensers can be collected and circulated separately. In general, however, substreams of the combined condensate are pumped into both condensers. In a preferred embodiment, the condensate is fed into the fifth or sixth condenser via the feeding vapor pipe in each case. Preferably, the condensate is introduced by jetting into the vapor pipe in the opposite direction to the gas stream, with the nozzle appropriately installed in the vapor pipe in the region of the condenser inlet. The amount of condensate which is recycled into the fifth condenser is preferably about 5 to 10 times the amount of the stream discharged. The amount of condensate which is recycled into the sixth condenser is preferably about 0.1% to 5% of the condensate recycled into the first condenser.

The temperature of the coolant of the sixth condenser is about 30 to 60° C. lower than that of the fifth condenser, in which the coolant has a temperature in the range from about 10 to 35° C.

The fifth temperature is preferably 0 to 45° C., preferably 5 to 35° C., below the condensation temperature of the tert-butyl ester at the fifth pressure and the sixth temperature is 45 to 80° C., preferably 50 to 65° C., even more preferably 50 to 55° C., below the condensation temperature of the tert-butyl ester at the sixth pressure.

The sixth temperature is at least 5° C. below the fifth temperature. Preferably, the sixth temperature is at least 10° C., more preferably at least 20° C., even more preferably at least 30° C. and most preferably at least 40° C. below the first temperature.

The fifth pressure is preferably in the range from 10 to 200 mbar abs., more preferably in the range from 30 to 100 mbar abs., even more preferably in the range from 50 to 90 mbar abs. The sixth pressure is preferably in the range from 10 to 200 mbar abs., more preferably in the range from 30 to 100 mbar abs., most preferably in the range from 50 to 90 mbar abs. Usually, the fifth and sixth condensers are connected on the gas side. In that case, the fifth and sixth pressures are the same.

The purity of the target ester obtained is typically 99.5% to 99.9% by weight of target ester.

Startup and Maintenance of the Reactor

In the steady state, the reactants are present as a solution in the target ester, which allows homogenization of the reaction and particularly advantageous removal of heat. To start up the reactor, the reactor is therefore preferably filled with the target ester. Thereafter, the reactants and catalyst are introduced into the reactor and the reaction commences.

On startup of the plant, the reactor contents are preferably passed into a collecting vessel. The collecting vessel is disposed at the geodetically lowest point of the plant and is connected to the reactor via separate lines. In the case of a leak, rapid emptying of the reactor is thus possible. Typically, no pumping systems are needed for the purpose. The collecting vessel has a pressure equalization means and has been filled with an oxygenous gas having an oxygen content of 10% by volume of oxygen or less, preferably 5% by volume of oxygen or less, in inert gas, preferably nitrogen. The collecting vessel is cooled by means of a pump and an external heat exchanger. The contents of the collecting vessel can then be worked up further independently.

The reactants, especially the $C_1$-$C_4$ carboxylic acid, are preferably used in substantially anhydrous form. The surfaces in contact with the reaction components in the process preferably consist of materials matched to the corrosivity of the carboxylic acid used in terms of technical corrosion resistance, for example stainless steel of the 1.4541 or 1.4571 quality, or stainless steels at least equivalent to these in terms of corrosion characteristics. Because of the very low water content in the process system, even when strong inorganic acids are used as catalyst, there is no corrosive attack beyond the extent of the industrially relevant resistance in the case of these materials. In production plants for ethylenically unsaturated esters, it is typically necessary to clean with hot sodium hydroxide solution, as a result of which the materials used experience alternating stress between organic acid and sodium hydroxide cleaning medium. The use of what are called duplex steels such as 1.4462 may therefore be advantageous for improved long-term stability of the apparatus.

Especially in the regions where there are additionally also a high temperature and mechanical stress in addition to the described corrosive stress by inorganic acids and a strong inorganic acid as catalyst, as in the thin-film evaporator for removal of the acidic catalyst from the majority of the organic matter, it is advantageous to use materials having much better corrosion resistance, for example nickel-base materials such as 2.4602, 2.4605, 2.4610 or 2.4819. Not only has experience shown that these materials have a longer service life, but they additionally also have considerable reserves in the event of unplanned occurrence of water as corrosion-promoting agent because of even smaller rates of corrosive material removal compared to the stainless steels. The use of these materials allows advantageous emergency operation properties without any risk of rapid total loss of apparatuses. In a departure from standard operation, water may be present into the system, for example, as a result of temporary unintentional introduction, for example via water-contaminated feedstocks or auxiliaries, as a result of a leak in the reactor cooling or in the condensers used in the fractional condensation, or because of a steam leak into the process in the apparatuses heated directly with steam.

To clean the reactor, the emptied reactor is preferably filled with sodium hydroxide solution (e.g. 5% by weight in demineralized water) which has been heated to about 80° C. and the solution is circulated in the reactor. The cooled aqueous alkali remaining after the cleaning is discarded, optionally after a suitable treatment for release into a wastewater treatment unit (for example a water treatment plant). After the reactor has been cleaned, especially freed of organic soiling, residues of the solution in the reactor system or further cleaned plant components may be removed by means of flushing with water.

Safety Devices

Isobutene is highly flammable and can form chemical explosive mixtures in the presence of oxygen, which can ignite at hot surfaces in the presence of particular oxygen concentrations. In standard operation, the plant is suitably operated in startup and shutdown operations in such a way that the oxygen concentration in the gas phase at any time is below the oxygen concentration required for an explosion. For this purpose, the plant is purged and filled prior to startup preferably with an oxygenous gas having an oxygen content of 10% by volume of oxygen or less, preferably 6% by volume of oxygen or less, in a mixture with an inert gas, preferably nitrogen. Preferably, the oxygenous gas is what is called lean air having an oxygen content of 10% by volume of oxygen or less, produced, for example, by suitable dilution of air with molecular nitrogen, for example. All components to be supplied to the process are preferably fed in under a lean air atmosphere. Complete exclusion of oxygen is undesirable particularly when one of the stabilizers elucidated hereinafter requires oxygen to be effective. If oxygen is consumed during the process, fresh lean air is preferably fed in continuously at suitable points, for example into the bottom of the second distillation column. The use of lean air prevents the gas composition from passing through an explosive range even in the event of inhomogeneities in the composition.

In order to detect leaks of air, especially into the plant components operated under reduced pressure, online oxygen meters are preferably installed at various points in the plant. More preferably, these online oxygen meters are installed in the lines for the noncondensable vapors from the fractional condensations.

The reactor is completely filled with liquid and is therefore preferably safeguarded against thermal expansion by a safety valve. In addition, the reactor preferably has a rapid isolation, emptying and decompression system (SAFES), by means of which the entire reactor contents, in the event of a leak, can be discharged without contact with the environment into a vented collecting vessel which can be ventilated and evacuated safely in terms of the explosion risk. The contents of this collecting vessel can preferably be cooled by means of a heat exchanger, in order to be able to remove any heat arising from further reaction in a controlled manner. The collecting vessel and its dedicated devices are configured in such a way that the contents thereof can preferably be fed back to the process at suitable points.

Stabilizer Addition

The $C_1$-$C_4$ carboxylic acids used in the present process, when they are carboxylic acids having ethylenically unsaturated groups, may have a high tendency to polymerize, particularly at relatively high temperature. Especially in the case of distillations, these compounds are generally exposed to temperatures which can easily trigger an unwanted free-radical polymerization. This firstly results in the soiling of the apparatus, the blockage of lines and pumps, and deposition on column trays and heat exchange surfaces. The cleaning of the plants is an inconvenient, costly and environmentally polluting operation, and the availability of the plants is greatly reduced as a result. Secondly, uncontrolled free-radical polymerizations can constitute a safety risk. The use of suitable stabilizers can prevent polymerizations of this kind.

To inhibit polymerization, stabilizers or inhibitors are typically used. The stabilizers are typically solids and are fed to the process in solution. The stabilizer solutions are preferably prepared batchwise.

Suitable stabilizers are, for example, N-oxyl compounds, nitroso compounds, phenol compounds, phenothiazines or mixtures thereof. The polymerization-inhibiting action of the stabilizers is generally enhanced by the presence of molecular oxygen. In some cases, the presence of molecular oxygen is absolutely necessary for the efficacy of the stabilizer. It is therefore preferable that molecular oxygen is present in the plant.

Suitable N-oxyl compounds include 1-oxyl-2,2,6,6-tetramethylpiperidine (TEMPO), 1-oxyl-2,2,6,6-tetramethyl-piperidin-4-ol (4-HT), 1-oxyl-2,2,6,6-tetramethylpiperidin-4-one, 1-oxyl-2,2,6,6-tetramethyl-4-n-propoxypiperidine, 1-oxyl-2,2,6,6-tetramethyl-4-(2-methoxyethoxy)piperidine, 1-oxyl-2,2,6,6-tetramethyl-4-(2-methoxyethoxyacetoxy)-piperidine; 1-oxyl-2,2,6,6-tetramethylpiperidin-4-yl stearate, 1-oxyl-2,2,6,6-tetra-methylpiperidin-4-yl acetate, 1-oxyl-2,2,6,6-tetramethylpiperidin-4-yl butyrate, 1-oxyl-2,2,6,6-tetramethylpiperidin-4-yl 2-ethylhexanoate, 1-oxyl-2,2,6,6-tetramethylpiperidin-4-yl octanoate, 1-oxyl-2,2,6,6-tetramethylpiperidin-4-yl laurate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, 1-oxyl- 2,2,6,6-tetramethyl-4-allyloxypiperidine, 1-oxyl-2,2,6,6-tetramethyl-4-acetamidopiperidine, 1-oxyl-2,2,6,6-tetramethyl-4-(N-butylformamido)piperidine, N,N'-bis(1-oxyl-2,2,6,6-tetramethyl-piperidin-4-yl)adipamide, N-(1-oxyl-2,2,6,6-tetramethylpiperidin-4-yl)caprolactam, N-(1-oxyl-2,2,6,6-tetramethylpiperidin-4-yl)-dodecylsuccinimide, 2,4,6-tris-(N-butyl-N-(1-oxyl-2,2,6,6-tetramethylpiperidin-4-yl]-s-triazine, 4,4'-ethylenebis(1-oxyl-2,2,6,6-tetramethyl-piperazin-3-one), 1-oxyl-2,2,6,6-tetramethyl-4-(2,3-dihydroxypropoxy)piperidine, 1-oxyl-2,2,6,6-tetramethyl-4-(2-hydroxy-4-oxapentoxy)piperidine, di-tert-butylnitroxyl and 4,4',4''-tris-(2,2,6,6-tetramethylpiperidinooxyl) phosphite.

1-Oxyl-2,2,6,6-tetramethylpiperidin-4-ol (4-HT) is particularly suitable.

Suitable nitroso compounds include nitrosophenol, N-nitrosodiphenylamine, isoamyl nitrite, N-nitrosocyclohexylhydroxylamine, N-nitroso-N-phenylhydroxylamine and salts thereof.

Suitable phenol compounds include hydroquinone, 2-methoxyphenol, 3-methoxyphenol, 4-methoxyphenol (MEHQ), 2-ethoxyphenol, 3-ethoxyphenol and 4-ethoxyphenol. 4-Methoxyphenol (MEHQ) is particularly suitable.

Suitable phenothiazines comprise phenothiazine (PTZ), 2-methylphenothiazine, 2-octylphenothiazine, 2-nonylphenothiazine, 2,8-dimethylphenothiazine, 3,7-dimethyl-phenothiazine, 3,7-diethylphenothiazine, 3,7-dibutylphenothiazine, 3,7-dioctylphenothiazine and 2,8-dioctylphenothiazine, 3,7-dinonylphenothiazine, 2,8-dinonylphenothiazine, 2-($\alpha,\alpha$-dimethylbenzyl) phenothiazine, 3,7-bis($\alpha,\alpha$-dimethylbenzyl)phenothiazine and 2,8-bis($\alpha,\alpha$-dimethylbenzyl)phenothiazine. Phenothiazine (PTZ) is particularly suitable.

It is also possible to use a plurality of stabilizers at once. The stabilizers are generally employed in amounts of about 2 to 2000 ppm, based on the total amount of carboxylic acid and isobutene.

In a preferred manner, the stabilizer is added in solution in a solvent. Suitable solvents in principle are all of those in which the particular stabilizer is soluble and which is miscible with the liquid phase to be stabilized. In order to avoid contamination with (external) solvents not required in the process in the first place, or the requirement for removal of an external solvent, the solvent used is preferably a liquid present in the process in any case. Particular preference is given to using the pure target ester as solvent.

The stabilizer is typically introduced by means of quantitatively controlled supply by means of pumps; preferably, the stabilizer solution, for better distribution, is sprayed in by means of spray devices such as spray nozzles.

Some of stabilizers mentioned are effective only in the presence of oxygen, one example being MEHQ, as a result of which a relatively high oxygen concentration as present in air, for example, would be advantageous. On the other hand, the oxygen concentration should be limited to comparatively low values in order that no explosive mixtures occur. The process is suitably conducted in such a way that the oxygen concentration in the gas phase at all relevant points and at any time is below the explosion limit. Preferably, the oxygen concentration in all the gaseous mixtures is preferably in the range from 3% to 8% by volume.

The tendency to polymerize exists particularly in the liquid phase at reduced concentrations of stabilizers and optionally oxygen. Since the stabilizers are generally nonvolatile, they accumulate in the bottom of the particular evaporation system in evaporation steps. It is therefore normally necessary to add stabilizer again after the evaporation of polymerizable compounds when the compounds are condensed, since the condensate is generally obtained very substantially free of stabilizers.

The process of the invention encompasses a multitude of process steps in which substance mixtures having very different compositions are present under a wide variety of different process conditions. To assure safe and economically viable operation, it is necessary to vary the stabilizers added in each case, which can be introduced into the process at various points.

In a preferred embodiment, in the case of reaction of the $C_1$-$C_4$ carboxylic acid with isobutene, a stabilizer selected from phenothiazines, more preferably PTZ, is present. The (meth)acrylic acid used may already have been pre-stabilized with PTZ, which is advantageous especially in the startup of the plant. Further amounts of PTZ can be metered into the reactor. In the partial evaporation b) of the esterification mixture, PTZ is distilled over together with the acidic catalyst into the liquid high boiler phase, which is separated from the product-containing main stream. The liquid high boiler phase is preferably recycled back into the reactor, such that it is generally necessary to supply the process continuously only with small supplementary amounts of fresh PTZ.

In a preferred embodiment, a stabilizer selected from N-oxyl compounds is added in the fractional condensation c). More preferably, a solution of 4-HT in target ester is added. The stabilizer is preferably added at the vapor entry into the first condenser. Together with a recycle stream of the condensate at the vapor entry of the second condenser, this stabilizer also passes into the second condenser.

The first distillation column is likewise stabilized with a stabilizer selected from N-oxyl compounds, more preferably 4-HT. The feed stream into the first distillation column comprises 4-HT from the preceding step, and a further amount of 4-HT is added at the top of the column, especially at the vapor entry of the third condenser, and passes into the first distillation column as well together with the condensate reflux.

In a preferred embodiment, a stabilizer selected from N-oxyl compounds, more preferably 4-HT, is added to the feed to the second distillation column.

The bottom and the stripping section of the second distillation column are stabilized by the N-oxyl compound. It is preferable not to stabilize the rectifying section of the second distillation column with N-oxyl compounds, since it would not be possible to entirely prevent such compounds from passing over. The N-oxyl compounds are undesirable in the target ester because they can lead to discoloration of the product and substances produced therefrom. Therefore, in the rectifying section of the second distillation column, a stabilizer selected from phenol compounds, especially MEHQ, is added. This stabilizer is also used for stabilization of the product and therefore does not have any adverse effect, i.e. need not be removed in a later step. MEHQ is preferably added to the circulation stream via the condensers and/or to the condensate reflux stream into the second distillation column. Appropriately, this is accomplished by injection via a nozzle installed centrally in the vapor pipe outlet.

In order to assure the efficacy of the MEHQ, a molecular oxygen-comprising gas, preferably lean air (5% by volume of oxygen in nitrogen), is fed into the bottom of the second distillation column. These measures make it possible to prevent polymer formation in the condensers, the vapor pipes and the column, or at least to prevent it to such an extent that economically advantageous long operation run times without shutdowns for cleaning are possible.

The invention is illustrated in detail by the appended FIGURE.

FIG. 1 is a schematic diagram of a plant suitable for performance of the process of the invention.

According to FIG. 1, by means of a mixer M1, an aliphatic $C_1$-$C_4$ carboxylic acid, a stabilizer I1 and the acidic catalyst are fed as a mixture to reactor R1 via a line 1 and a nozzle E1 (not shown in FIG. 1). Isobutene is introduced into the bottom of reactor R1. Via the nozzle E1, the reactor R1 is also supplied with the isobutene-containing uncondensed vapors B3 and B6 from condensers C2 and C4. The condensate from the reflux condenser W1 is fed to reactor R1.

In the reactor R1, the addition reaction of isobutene and the aliphatic $C_1$-$C_4$ carboxylic acid takes place. The reactor has four cooled reaction zones. The reaction zones are separated from one another by dividing sheets, the transition from one reaction to the next consisting of a hole of low cross section. The reactants are mixed in the reactor by means of a nozzle E1 and by swirling at the transition from one zone to the next.

The liquid reaction product G1 is drawn off at the top of the reactor R1 by means of a level regulator, so as to establish a constant liquid/gas phase boundary. The gas phase consisting essentially of inert gases, isobutene and small amounts of the tert-butyl ester is fed to the reflux condenser W1 via line 2. The condensate from the reflux condenser W1 comprises isobutene and acrylic acid and is fed via line 3 to reactor R1. The gas phase from the reflux condenser W1 is discharged from the process as offgas via line 4.

The liquid reaction product G1 is drawn off from the side at the top of reactor R1 and fed under quantitative control to the evaporation unit V1 consisting of a falling-film evaporator and a separation vessel (not shown individually in FIG. 1). The pressure of the liquid reaction product is lowered by means of a throttle valve (not shown in FIG. 1) from reactor pressure to reduced pressure, at which the catalyst removal that follows is effected. In the falling-film evaporator of the evaporation unit V1, the reaction mixture is partially evaporated and conducted onward into the separation vessel. The separation vessel preferably comprises a droplet separator in order to reliably remove entrained high boiler components such as sulfuric acid and the stabilizer I1. The non-gaseous constituents are collected in the separation vessel as the first high boiler phase SPh1 and cooled by means of an external cooler (not depicted in FIG. 1) in order to prevent any reverse reaction of the tert-butyl ester present therein to the carboxylic acid and isobutene.

A portion of the first high boiler phase SPh1 is fed under quantitative control to the thin-film evaporator V2, in order to enable the further removal of carboxylic acid or tert-butyl ester in gaseous form. The gas phase produced in the thin-film evaporator V2 is recycled into the separation vessel of the evaporation unit V1 via line 5, while a portion of the liquid second high boiler phase SPh2 is conducted into the settling vessel A1. Preferably, substreams of the second high boiler phase SPh2 are used to preheat the feed stream to the thin-film evaporator of the evaporation unit V1. By varying the hot substreams, it is possible to vary the composition of the feed stream to the thin-film evaporator of the evaporation unit V1 and the temperature of the feed stream.

A further portion of the first high boiler phase SPh1 and a further portion of the second high boiler phase SPh2 are recycled into reactor R1 together or in each case individually under quantitative control via the nozzle E1 (the recycling of the second high boiler phase SPh2 is not depicted in FIG. 1).

The gaseous constituents from the separation vessel of the evaporation unit V1 are fractionally condensed in condensers C1 and C2, the vapor B2 from condenser C1 being conducted into condenser C2. A stabilizer I2 is added at the top of the condenser C1 and a stabilizer I3 is added at the top of the condenser C2. For the cooling of the condenser C1, it is possible to use, for example, river water or cooling water at the same temperature level, while condenser C2 is operated with brine cooling. The vapor B3 not condensed in the condenser C2 is conducted into the reactor R1 via nozzle E1.

The condensates K1 and K2 obtained in the condensers C1 and C2 are combined and fed to the side of the distillation column D1. In the distillation column D1, low boilers, particularly diisobutene and isobutene, are removed. The bottom of the distillation column D1 is heated by means of a circulation evaporator (not shown in FIG. 1), by means of which a portion of the bottoms is pumped in circulation. The low boilers B4 are removed in vaporous form at the top of the distillation column D1 and fractionally condensed in the condensers C3 and C4. The vapor B5 from the condenser C3 is conducted into the condenser C4. For the cooling of the condenser C3, it is possible, for example, to use river water or cooling water at the same temperature level, while condenser C4 is operated with brine cooling. The vapor B6 uncondensed in the condenser C4 is conducted via the nozzle E1 into the reactor R1. A stabilizer I4 is added at the top of the condenser C3. The condensates K3 and K4 obtained in the condensers C3 and C4 are combined; a substream is conducted into the distillation column D1 as reflux stream; the remainder is fed to the settling vessel A2.

The bottom stream S1 from the distillation column D1 is fed to the side of the distillation column D2. Stabilizer I5 is metered into the feed to the distillation column D2. The bottom of the distillation column D2 is heated by means of a circulation evaporator (not shown in FIG. 1), through which a portion of the bottoms is pumped in circulation. In the course of pumped circulation, the bottom of the distillation column D2 is also supplied with lean air.

In the distillation column D2, the tert-butyl ester is separated from the remaining aliphatic carboxylic acid. Typically, the boiling point of the carboxylic acid is above the boiling point of the tert-butyl ester, and for that reason the pure tert-butyl ester is drawn off via the top and the carboxylic acid is obtained at the bottom of the distillation column D2. In order to avoid condensation of the tert-butyl ester at the top of the column, the top of the column is heated with steam. Thus, any polymerization of the tert-butyl ester resulting from the condensation is also prevented. The bottom stream S2 from the distillation column D2 is recycled into the reactor R1 via a heat exchanger (not shown in FIG. 1).

The vapor B7 from the distillation column D2 is fractionally condensed in condensers C5 and C6; the vapor B8 from condenser C5 is conducted into condenser C6. A stabilizer I7 is added at the top of the condenser C5 and a stabilizer I8 is added at the top of the condenser C6. The vapor B9 uncondensed in the condenser C6 is discharged from the process as offgas. The offgas is sent, for example, to a flare or an offgas incineration.

A substream of the combined condensates P1 and P2 from condensers C5 and C6 is introduced into the condensers C5 and C6 (not shown in FIG. 1) or, with addition of the stabilizer I6, as reflux stream into the distillation column D2. A further substream of the combined condensates P1 and P2 from the condensers C5 and C6 is discharged from the process as pure tert-butyl ester via a heat exchanger (not depicted in FIG. 1). For storage stabilization, further stabilizer I9 can be added to the pure tert-butyl ester.

The plant preferably has a rapid isolation, emptying and decompression system (SAFES), by means of which, in the event of a leak, the entire contents of the reactor R1 can be discharged into a vented collecting vessel (not shown in FIG. 1). The contents of this collecting vessel can be cooled by means of a heat exchanger, in order to be able to remove the heat that arises from further reaction. The contents of the collecting vessel can be fed back to the process at various points, especially the reactor R1, the falling-film evaporator V2 or the thin-film evaporator of the evaporation unit V1.

EXAMPLE 1

The example which follows was conducted in a plant according to FIG. 1. All the percentages stated are based on weight, unless stated otherwise. Acrylic acid and isobutene were converted to tert-butyl acrylate with addition of sulfuric acid. The plant was purged and filled with lean air (5% by volume of oxygen in nitrogen).

Acrylic acid (AA, 99.95% with 0.05% acetic acid, 0.79 m$^3$/h) was mixed in a mixer M1 with acrylic acid recycled from the bottom of distillation column D2 (93.12% AA, 4.60% high boilers, 0.52 m$^3$/h) and with a phenothiazine (PTZ) solution (97.95% AA, 2.00% PTZ, 0.01 m$^3$/h) as stabilizer I1. Sulfuric acid (technical grade, 96%, 3.3 kg/h) was metered in by means of nitrogen (3.5 bar abs.). Also fed to the mixture was a substream (2235 kg/h) of the liquid phase from the separation vessel of the evaporation unit V1.

The liquid reactants and return streams were fed as a mixture via line 1, a cooler (shell and tube system, 180 m$^2$, 1.4571 stainless steel, not shown in FIG. 1) and nozzle E1 to reactor R1, a cascaded bubble column. The cooler exit temperature is 29° C.

Isobutene (654 kg/h) was metered directly into the bottom of the reactor. Also metered into reactor R1, via the nozzle E1, were the isobutene-containing vapors B3 and B6 from condensers C2 and C4 (105 m$^3$/h), together with the tert-butyl acrylate-containing condensate from the reflux condenser W1. The nozzle E1 was an ejector jet nozzle. In the nozzle, the pressure was increased by the motive jet to about 2 bar abs.

The reactor R1 had four reaction zones, and the transition consisted of a hole of small cross section (diameter 24 mm). The reaction zones were each cooled (zone 1: external river water cooler, 121 kW; zone 2: external brine cooler, 28 kW; zone 3: internal brine cooler, 14 kW; zone 4: internal brine cooler, 14 kW; the temperature of each of the brines was −20° C.). In the reactor R1, the slightly exothermic addition reaction (−37.6 kJ/mol) of isobutene and acrylic acid took place at a temperature of 31° C. in zone 1, 25° C. in zone 2, 20° C. in zone 3 and 18° C. in zone 4, and a pressure of 1.93 bar abs.

The reactants were mixed in the reactor firstly by means of the nozzle E1 and secondly by means of swirling at the transition from one zone to the next. At the top of the reactor (zone 4), by means of closed-loop level control, a liquid/gas phase boundary was established.

The gas phase comprised 25.20% isobutene, 0.23% tert-butyl acrylate (TBA) and inert gases, and was conducted into the reflux condenser W1 via line 2. The TBA entrained in the offgas was condensed out by means of reflux condenser W1 and recycled into the reactor R1 via line 3 in a mixture with isobutene-containing vapors from condensers C2 and C4 via nozzle E1. The pressure at the top of the reactor R1 in the offgas line was adjusted to 1.2 bar abs. At the bottom of the reactor, a pressure of 1.93 bar abs. was established. The gaseous constituents from the reflux condenser W1 (3.77 m$^3$/h) were discharged from the process via line 4.

The liquid reaction product from the reactor R1 had the following composition:

| | |
|---|---|
| 4.90% | isobutene |
| 33.51% | AA |
| 54.00% | TBA |
| 1.00% | diisobutene |
| 3.71% | high boilers |
| 1.56% | sulfuric acid |
| 1.32% | other constituents |

The liquid reaction product from the reactor R1 (4.83 m$^3$/h, 18° C.) was removed at the upper end of the reactor R1 and fed via a screen basket filter (0.1 m$^2$, not depicted in FIG. 1) to the falling-film evaporator (70° C., 309 kW, 47 m$^2$) of the evaporation unit V1. By means of a closed-loop control valve (flow regulation), the pressure was reduced to 60 mbar abs. A biphasic mixture formed as a result of the evaporation of a portion of the low boiler components. In the falling-film evaporator of the evaporation unit V1, the biphasic mixture was evaporated further under temperature control at 54.4° C. and 70 mbar abs. and then passed into the separation vessel of the evaporation unit V1. The separation vessel was equipped with a droplet separator in order to reliably remove sulfuric acid and PTZ.

The non-gaseous constituents in the separation vessel of the evaporation unit V1 were cooled to −2° C. by means of a brine cooler via a pumped circulation stream as the first high boiler phase SPh1. In the separation vessel, a mixing temperature of about 4 to 5° C. was established. A portion of the pumped circulation stream (2235 kg/h) of the first high boiler phase SPh1 was fed back to the reactor R1 for sulfuric acid recycling. In addition, a portion of the pumped circulation stream of the first high boiler phase SPh1 (106 kg/h) was fed to the thin-film evaporator V2 (4 m$^2$, nickel-chromium-molybdenum alloy 2.4610), in order to remove further products of value (TBA, AA) via the top of the thin-film evaporator V2 (70° C., 60 mbar abs.). The thin-film evaporator V2 was heated by means of low-pressure steam. Connected downstream of the bottoms output of the thin-film evaporator V2 was a pump (not shown in FIG. 1), which conducted the second high boiler phase SPh2 for discharge into a substream to the settling vessel A1. On the way to the settling vessel A1, the substream SPh2 of the second high boiler phase was cooled from 70° C. to 35° C. This was effected by means of a jacketed pipe through which water at a temperature of 30° C. was conducted in countercurrent.

A further substream of the second high boiler phase SPh2 from the thin-film evaporator V2 was in turn added as a recycle stream directly to the feed stream to the thin-film evaporator V2. By varying the hot recycle stream flow rate, it was possible to adjust the feed stream and the feed stream temperature within a wide range. In conjunction with the adjustment of the amount of heating steam and a heating steam temperature, the thin-film evaporator V2 was capable of covering a large load range.

Yet a further substream of the second high boiler phase SPh2 from the thin-film evaporator was added to the cold pumped circulation stream from the suction side of the pump to the thin-film evaporator V2, but the latter was warmed only to a minor degree as a result. The feed stream to the thin-film evaporator V2 was withdrawn on the pressure side of the pump.

The vapor from the thin-film evaporator V2 was fed via line 5 to the separation vessel of the evaporation unit V1. The vapor B1 from the separation vessel of the evaporation unit V1 (about 53° C.) had the following composition:

| | |
|---|---|
| 66% | TBA |
| 22% | AA |
| 10% | isobutene |
| 3% | other constituents |

The vapor B1 was fractionally condensed and, for this purpose, passed into the top of the condenser C1 (shell and tube heat exchanger, 75 m$^2$, cooling: river water (27° C.), 60 mbar abs., 1.4571 stainless steel). In the condenser C1 the mixture fed in was cooled to 29° C.

The vapor B2 from condenser C1 (comprising about 56% TBA, 5% AA, 36% isobutene) was conducted into the top of the condenser C2 (shell and tube heat exchanger, 30 m$^2$, cooling: cooling brine (−20° C.), 60 mbar abs., 1.4571 stainless steel). The condensate K2 from the condenser C2 (comprising about 84% TBA, 7% AA, 5% isobutene, about −17° C.) was combined in a vessel (not shown in FIG. 1) with the condensate K1 from the condenser C1. The vapor B3 from the condenser C2 (comprising about 95% isobutene) was mixed by means of a pump (not shown in FIG. 1) with the vapor B6 from the condenser C4 and recycled into the reactor R1.

The condensate K1 from the condenser C1 (comprising about 73% TBA, 24% AA, 0.5% isobutene) was combined in a vessel (not shown in FIG. 1) with the condensate K2 from the condenser C2. The combined condensate from C1 and C2 had the following composition:

| | |
|---|---|
| 72.70% | TBA |
| 23.93% | AA |
| 1.49% | diisobutene |
| 0.62% | isobutene |
| 1.26% | other constituents |

A substream of the combined condensates from C1 and C2 was passed together with a 4-hydroxy-TEMPO (4-HT) solution (2% in TBA) as stabilizer I2 into the top of the condenser C1, and a substream thereof in turn was passed as stabilizer I3 into the top of the condenser C2.

A further substream of the combined condensates from condensers C1 and C2 was fed to the distillation column D1 (40 dual-flow trays, 79° C. in the column bottom, 120 mbar abs. in the column head) to tray 23. The distillation column D1 was heated by means of a natural circulation evaporator (4 bar abs. steam). The temperature of the distillation column D1 was regulated by means of a regulating valve in the reflux line. The vacuum was regulated by means of a regulating valve in the suction line to the vacuum unit.

The vapor B4 from the distillation column D1 was fractionally condensed and, for this purpose, passed into the condenser C3 (shell and tube heat exchanger, 110 m$^2$, cooling: river water (27° C.), 120 mbar abs., 1.4571 stainless steel). In the condenser C3, the mixture fed in was cooled to 29° C. The condensate K3 from condenser C3 was combined in a vessel with the condensate K4 from condenser C4.

The vapor B5 from condenser C3 was passed into condenser C4 (shell and tube heat exchanger, 8 m$^2$, cooling: cooling brine (−20° C.), 120 mbar abs., 1.4571 stainless steel) and cooled to −2° C. The condensate K4 from condenser C4 was combined in a vessel (not shown in FIG. 1) with the condensate K3 from condenser C3. The vapor B6 from condenser C4 (147.7 m$^3$/h, 69.76% isobutene) was mixed by means of a pump (not shown in FIG. 1) with the vapor B3 from condenser C2 and the condensate from the reflux condenser W1 and recycled into the reactor R1.

A substream of the combined condensates C3 and C4 was passed into the top of the distillation column D1; a substream thereof in turn was passed as a mixture with a 4-HT solution (2% in TBA) as stabilizer I4 into the top of the condenser C3.

The bottom product from distillation column 1 had the following composition:

| | |
|---|---|
| 74.46% | TBA |
| 24.37% | AA |
| 1.17% | other constituents |

The bottom product S1 from distillation column D1 was admixed with a 4-HT solution (2% in TBA) as stabilizer I5 and fed to the distillation column D2 (40 dual-flow trays, 92° C. in the column bottom, 75 mbar abs. in the column head) to tray 18. The distillation column D2 was heated by means of a natural circulation evaporator (4 bar abs. steam). The temperature of the distillation column D2 was regulated by means of a regulating valve in the reflux line. The vacuum was regulated by means of a regulating valve in the suction line to the vacuum unit.

Metered into the bottom of distillation column D2 were 6 m$^3$/h of lean air (5% by volume of oxygen in nitrogen).

The vapor B7 from distillation column D2 (comprising 99.57% TBA) was fractionally condensed and, for this purpose, conducted into condenser C5 (shell and tube heat exchanger, 72 m$^2$, cooling: river water (27° C.), 70 mbar abs., 1.4571 stainless steel). In condenser C5, the mixture fed in was cooled to 29° C. The condensate P1 from condenser C5 was combined in a vessel (not shown in FIG. 1) with the condensate P2 from condenser C6.

The vapor B8 from condenser C5 was passed into the top of condenser C6 (shell and tube heat exchanger, 12 m$^2$, cooling: cooling brine (−20° C.), 65 mbar abs. 1.4571 stainless steel) and cooled to −17° C. The condensate P2 from condenser C6 was combined in a vessel (not shown in FIG. 1) with the condensate P1 from condenser C5 as the product. The vapor B9 from condenser C6 was discharged from the process by means of a pump (not shown in FIG. 1).

A substream of the combined condensates P1 and P2 from condensers C5 and C6 was passed into distillation column D2 as reflux with addition of 4-methoxyphenol (MEHQ, 2% in TBA) solution as stabilizer I6. Further substreams of the combined condensates P1 and P2 from condensers C5 and C6 were fed to condensers C5 and C6 respectively with addition of 4-methoxyphenol (MEHQ, 2% in TBA) solution as stabilizers I7 and I8.

In this case, the stabilization of the column was undertaken with a higher content of MEHQ, while the 4-methoxyphenol content in condensers C5 and C6 was 15+/−5 ppm. In order to avoid the condensation of TBA at the top of distillation column D2, which could also lead to polymerization of TBA, the top of the column was heated with steam (4 bar abs.).

Yet a further substream of the combined condensates P1 and P2 from condensers C5 and C6, after the pressure had been increased to 4 bar abs., was cooled to 20° C. by means of a heat exchanger (spiral heat exchanger, cooling: cooling brine (−20° C.), not shown in FIG. 1) and discharged from the process as product. A substream thereof was used as solvent for the 4-HT and MEHQ stabilizers.

The product had the following composition:

| 99.83% | TBA |
|---|---|
| 0.05% | isobutene |
| 0.02% | tert-butyl propionate |
| 15 ppm | MEHQ |

The bottoms S2 from distillation column D2 (comprising 93.12% AA), after the pressure had been increased to 4 bar abs., was cooled to 30° by means of a heat exchanger (spiral heat exchanger, 5 m², cooling: warm water, 1.4571 stainless steel, not shown in FIG. 1), and a substream was combined with the feed stream of the acrylic acid and fed to reactor R1.

The reduced pressure required in the evaporation unit V1 and the downstream units was generated by means of a vacuum unit. Roots piston compressors without lubricant oil were used.

For preparation of the stabilizer solution of phenothiazine, acrylic acid in pure form was initially charged in a stirred vessel (trace-heated with water, 30° C., vented). PTZ was introduced in solid form by means of a sack emptying station and a pneumatic powder transfer system by means of application of reduced pressure via a pump. Small amounts of lean air (5% by volume of oxygen in nitrogen) were added. PTZ was dissolved while stirring and the PTZ solution was passed into a reservoir vessel (trace-heated with water, 30° C., vented), from which the metered addition into the process was undertaken.

For preparation of the stabilizer solution of 4-hydroxy-2,2,6,6-tetramethyl-1-oxyl-piperidine, tert-butyl acrylate (from the combined condensates P1 and P2 from condensers C5 and C6) was initially charged in a stirred vessel (vented). 4-HT was introduced into the stirred vessel in solid form by means of a sack emptying station and a pneumatic powder transfer system by means of application of reduced pressure via a pump. Small amounts of lean air (5% by volume of oxygen in nitrogen) were added. 4-HT was dissolved while stirring and the 4-HT solution was passed into a reservoir vessel (vented), from which the metered addition into the process was undertaken.

For preparation of the stabilizer solution of 4-methoxyphenol, tert-butyl acrylate (from the combined condensates P1 and P2 from condensers C5 and C6) was initially charged in a stirred vessel (vented). MEHQ was introduced into the stirred vessel in solid form by means of a sack emptying station and a pneumatic powder transfer system by means of application of reduced pressure via a pump. Small amounts of lean air (5% by volume of oxygen in nitrogen) were added. MEHQ was dissolved while stirring and the MEHQ solution was passed into a reservoir vessel (vented), from which the metered addition into the process was undertaken.

The brine used in the brine coolers was set up as a pressure circuit. The brine was cooled in an ammonia refrigeration system to −20° C. and fed to the respective process elements. Thereafter, the brine was homogenized in a brine reservoir and fed by means of a pump back to the ammonia refrigeration system. The brine system had a balancing vessel blanketed with lean air (5% by volume of oxygen in nitrogen).

Unutilizable offgas obtained in the process was conducted through a separator and the uncondensed constituents were incinerated in a shielded flare, while the condensate was discharged.

It is clear that the process allows the preparation of tert-butyl acrylate in high purity (99.94% here) with simultaneously energetically favorable removal of isobutene, which was isolable with a high level of separation from the esterification mixture.

EXAMPLE 2a

The first vapor B1 was partially condensed in two stages (at two different temperatures) or in one stage, and the composition of the condensate and of the uncondensed vapor was examined. All percentages stated are based on weight, unless stated otherwise. The vapor B1 (about 53° C.) had the following composition:

| 1486 kg/h | (66%) | TBA |
|---|---|---|
| 494 kg/h | (22%) | acrylic acid |
| 218 kg/h | (10%) | isobutene |
| 58 kg/h | (3%) | other constituents |

The two-stage partial condensation was conducted at 33° C. or −18° C. (temperature of the respective condensates). Chosen as a comparison was a one-stage partial condensation at −18° C.

The cooling power for the two-stage partial condensation totalled 255 kW (202 kW for the first partial condensation conducted in condenser C1 and 53 kW for the second partial condensation conducted in condenser C2). The cooling power for the one-stage partial condensation was 311 kW. It is clear that the cooling power required is lower in the case of a two-stage partial condensation than in the case of a one-stage partial condensation.

The compositions of the respective condensates and vapors are reported in table A.

TABLE A

|  | T [° C.] | | Volume flow rate [kg/h] | Composition [% by wt.] |
|---|---|---|---|---|
| Two-stage partial condensation | | | | |
| Condensate 1st condenser | 33.0 | isobutene | 9 | 0.5 |
| | | acrylic acid | 462 | 27.2 |
| | | tert-butyl acrylate | 1180 | 69.6 |
| Vapor 1st condenser | 33.0 | isobutene | 209 | 37.3 |
| | | acrylic acid | 32 | 5.7 |
| | | tert-butyl acrylate | 306 | 54.6 |
| Condensate 2nd condenser | −18.0 | isobutene | 19 | 5.0 |
| | | acrylic acid | 32 | 8.3 |
| | | tert-butyl acrylate | 321 | 83.6 |
| | | other constituents | 12 | 3.1 |
| Vapor 2nd condenser | −18.0 | isobutene | 190 | 96.0 |
| | | acrylic acid | 0 | 0.0 |
| | | tert-butyl acrylate | 6 | 3.0 |
| Combined condensates | 23.9 | isobutene | 28 | 1.4 |
| | | acrylic acid | 494 | 23.7 |
| | | tert-butyl acrylate | 1500 | 72.2 |
| One-stage partial condensation | | | | |
| Vapor | −18.0 | isobutene | 97 | 96.7 |
| | | acrylic acid | 0 | 0.1 |
| | | tert-butyl acrylate | 2 | 2.4 |
| Condensate | −18.0 | isobutene | 121 | 5.6 |
| | | acrylic acid | 493 | 22.9 |
| | | tert-butyl acrylate | 1483 | 68.8 |

It is clear that the combined condensates from the two-stage partial condensation comprised a lower isobutene content than the condensate from the one-stage partial condensation. Correspondingly more isobutene was present in the vapor from the 2nd condenser of the two-stage partial condensation than in the vapor from the one-stage partial condensation. The two-stage partial condensation at a first temperature and a second, lower temperature achieves a higher separation sharpness overall than a one-stage partial condensation at the second temperature.

It is also clear that the temperature of the combined condensates from the two-stage partial condensation was higher than the temperature of the condensate from the one-stage partial condensation.

EXAMPLE 2b

The fourth vapor B4 was partially condensed in two stages (at two different temperatures) or in one stage and the composition of the condensate or the uncondensed vapor was examined. All the percentages stated are based on weight, unless stated otherwise. The vapor B4 (about 37° C.) had the following composition:

| | | |
|---|---|---|
| 55 kg/h | (5.3%) | isobutene |
| 18 kg/h | (1.8%) | water |
| 49 kg/h | (4.8%) | tert-butyl acrylate |
| 41 kg/h | (4.0%) | tert-butyl acetate |
| 744 kg/h | (72.5%) | diisobutene |
| 114 kg/h | (11.1%) | tert-butanol |

The two-stage partial condensation was conducted at 33° C. and −18° C. (temperature of the respective condensates). Chosen as a comparison was a one-stage partial condensation at −18° C.

The cooling power for the two-stage partial condensation totalled 126 kW (50 kW for the first partial condensation conducted in condenser C3 and 76 kW for the second partial condensation conducted in condenser C2). The cooling power for the one-stage partial condensation was 142 kW. It is clear that the cooling power required in a two-stage partial condensation is lower than in a one-stage partial condensation.

The compositions of the respective condensates and vapors are reported in table B.

TABLE B

| | T [° C.] | | Volume flow rate [kg/h] | Composition [% by wt.] |
|---|---|---|---|---|
| Two-stage partial condensation | | | | |
| Condensate 1st condenser | 33.0 | isobutene | 1 | 0.2 |
| | | tert-butyl acrylate | 43 | 8.6 |
| | | tert-butyl acetate | 23 | 4.7 |
| | | diisobutene | 376 | 74.6 |
| | | tert-butanol | 59 | 11.7 |
| Vapor 1st condenser | 33.0 | isobutene | 53 | 10.0 |
| | | tert-butyl acrylate | 17 | 3.11 |
| | | tert-butyl acetate | 18 | 3.4 |
| | | diisobutene | 367 | 69.0 |
| | | tert-butanol | 55 | 10.3 |
| Condensate 2nd condenser | −18.0 | isobutene | 42 | 8.1 |
| | | tert-butyl acrylate | 17 | 3.2 |
| | | tert-butyl acetate | 18 | 3.5 |
| | | diisobutene | 367 | 71.1 |
| | | tert-butanol | 55 | 10.7 |
| Vapor 2nd condenser | −18.0 | isobutene | 12 | 66.2 |
| | | tert-butyl acrylate | 0 | 0.1 |
| | | tert-butyl acetate | 0 | 0.1 |
| | | diisobutene | 1 | 7.2 |
| | | tert-butanol | 0 | 0.0 |

TABLE B-continued

| | T [° C.] | | Volume flow rate [kg/h] | Composition [% by wt.] |
|---|---|---|---|---|
| Combined condensates | 7.5 | isobutene | 43 | 4.2 |
| | | tert-butyl acrylate | 60 | 5.9 |
| | | tert-butyl acetate | 41 | 4.1 |
| | | diisobutene | 742 | 72.9 |
| | | tert-butanol | 114 | 11.2 |
| One-stage partial condensation | | | | |
| Vapor | −18.0 | isobutene | 5 | 48.7 |
| | | tert-butyl acrylate | 0 | 0.2 |
| | | tert-butyl acetate | 0 | 0.1 |
| | | diisobutene | 1 | 8.2 |
| | | tert-butanol | 0 | 0.0 |
| Condensate | −18.0 | isobutene | 49 | 4.8 |
| | | tert-butyl acrylate | 60 | 5.8 |
| | | tert-butyl acetate | 41 | 4.0 |
| | | diisobutene | 743 | 72.4 |
| | | tert-butanol | 114 | 11.1 |

It is clear that the combined condensates from the two-stage partial condensation comprised a lower isobutene content than the condensate from the one-stage partial condensation. The two-stage partial condensation allows a smaller isobutene loss via the low boiler removal compared to the one-stage partial condensation.

The invention claimed is:

1. A process for continuously preparing the tert-butyl ester of an aliphatic $C_1$-$C_4$ carboxylic acid, the process comprising:
   a) reacting the aliphatic $C_1$-$C_4$ carboxylic acid with isobutene in the presence of an acidic catalyst to give an esterification mixture (G1);
   b) partially evaporating the esterification mixture (G1) in a first distillation unit, giving a liquid first high boiler phase (SPh1) comprising the acidic catalyst, and a first vapor (B1) comprising the tert-butyl ester and unreacted isobutene;
   c) fractionally condensing the first vapor (B1) by partially condensing the first vapor (B1) at a first pressure and a first temperature and obtaining a first condensate (K1), partially condensing an uncondensed second vapor (B2) at a second pressure and a second temperature and obtaining a second condensate (K2) and an uncondensed third vapor (B3), comprising isobutene, the first temperature being 0 to 45° C. below the condensation temperature of the tert-butyl ester at the first pressure which is from 10 to 200 mbar abs and the second temperature being 45 to 80° C. below the condensation temperature of the tert-butyl ester at the second pressure which is from 10 to 200 mbar abs, with the proviso that the second temperature is at least 5° C. below the first temperature: and
   d) feeding a combination of the first condensate (K1) and the second condensate (K2) to a combined workup, and recycling the third vapor (B3) comprising isobutene into reaction a).

2. The process according to claim 1, in which the combined condensate is fed to a first distillation column (D1) wherein a first liquid bottom product (S1) and a fourth vapor (B4) comprising isobutene are obtained; the first liquid bottom product (S1) is fed to a further workup; the fourth vapor (B4) is fractionally condensed by partially condensing the fourth vapor (B4) at a third pressure and a third temperature and obtaining a first low boiler condensate (K3), an uncondensed fifth vapor (B5) comprising isobutene is partially condensed at a fourth pressure and a fourth temperature and a second low boiler condensate (K4) is obtained, the fourth temperature being lower than the third temperature; a sixth vapor (B6) comprising isobutene uncondensed at the fourth temperature is recycled into a); and the first and/or second low boiler condensate (K3) and (K4) is recycled partly as reflux to the top of the first distillation column (D1).

3. The process according to claim 2, wherein the third temperature is 5 to 40° C. below the condensation temperature of diisobutene at the third pressure and the fourth temperature is 30 to 55° C. below the condensation temperature of diisobutene at the fourth pressure, with the proviso that the fourth temperature is at least 5° C. below the third temperature.

4. The process according to claim 2, in which the first liquid bottom product (S1) is fed to a second distillation column (D2) to obtain a second liquid bottom product (S2) and a seventh vapor (B7); the second liquid bottom product (S2) is at least partly recycled into a); the seventh vapor (B7) is fractionally condensed by partially condensing the seventh vapor (B7) at a fifth pressure and a fifth temperature and obtaining a first product condensate (P1), an uncondensed eighth vapor (B8) is partially condensed at a sixth pressure and a sixth temperature and a second product condensate (P2) is obtained, the sixth temperature being lower than the fifth temperature; and the first and/or second product condensate (P1) and (P2) is recycled partly as reflux into the second distillation column (D2).

5. The process according to claim 4, wherein the fifth temperature is 0 to 45° C. below the condensation temperature of the tert-butyl ester at the fifth pressure and the sixth temperature is 45 to 80° C. below the condensation temperature of the tert-butyl ester at the sixth pressure, with the proviso that the sixth temperature is at least 5° C. below the fifth temperature.

6. The process according to claim 1, wherein the aliphatic $C_1$-$C_4$ carboxylic acid is acrylic acid, or methacrylic acid, or a mixture thereof.

7. The process according to claim 1, wherein the esterification mixture (G1) comprises 0.5% to 5.0% by weight of the acidic catalyst.

8. The process according to claim 1, wherein the acidic catalyst is an inorganic acid.

9. The process according to claim 1, wherein the acidic catalyst is an organic acid.

10. The process according to claim 1, wherein the reacting a) is conducted in the presence of a stabilizer which is at least one phenothiazine.

11. The process according to claim 1, wherein the fractional condensation c) is conducted in the presence of a stabilizer which is at least one N-oxyl compound.

12. The process according to claim 2, wherein the fractional condensation of the fourth vapor (B4) is conducted in the presence of a stabilizer which is at least one N-oxyl compound.

13. The process according to claim 12, wherein the stabilizer is added to the first liquid bottom product (S1).

14. The process according claim 4, wherein a stabilizer, which is at least one phenol compound, is metered into a rectifying section of the second distillation column (D2).

15. A process for continuously preparing the tert-butyl ester of an aliphatic $C_1$-$C_4$ carboxylic acid, the process comprising:
  aa) providing a plant comprising an esterification reactor, an evaporator, a first condenser and a second condenser;
  bb) purging and filling the plant with an oxygenous gas having an oxygen content of 10% by volume or less;
  a) reacting the aliphatic $C_1$-$C_4$ carboxylic acid with isobutene in the presence of an acidic catalyst to give an esterification mixture (G1);
  b) partially evaporating the esterification mixture (G1), giving a liquid first high boiler phase (SPh1) comprising the acidic catalyst, and a first vapor (B1) comprising the tert-butyl ester and unreacted isobutene:
  c) fractionally condensing the first vapor (B1) by partially condensing the first vapor (B1) at a first pressure and a first temperature and obtaining a first condensate (K1), partially condensing an uncondensed second vapor (B2) at a second pressure and a second temperature and obtaining a second condensate (K2), the first temperature being 0 to 45° C. below the condensation temperature of the tert-butyl ester at the first pressure which is from 10 to 200 mbar abs and the second temperature being 45 to 80° C. below the condensation temperature of the tert-butyl ester at the second pressure which is from 10 to 200 mbar abs, with the proviso that the second temperature is at least 5° C. below the first temperature; and
  d) feeding a combination of the first condensate (K1) and the second condensate (K2) to a combined workup, and a third vapor (B3) comprising isobutene not condensed at the second temperature is recycled into a).

16. The process according to claim 15, wherein the oxygenous gas having an oxygen content of 10% by volume or less is continuously fed into the plant ensure the presence of molecular oxygen in the plant.

17. The process according to claim 15, wherein the oxygen concentration in the gas phase at any point in the plant is maintained in the range from 3% to 8% by volume.

* * * * *